United States Patent
Gao et al.

(10) Patent No.: US 7,641,753 B2
(45) Date of Patent: Jan. 5, 2010

(54) PVC-FREE MULTILAYER TUBE WITH MORE DEPENDABLE PEELABILITY FOR MEDICAL PURPOSES, AND PROCESS FOR ITS PRODUCTION

(75) Inventors: Xiaogang Gao, St. Wendel (DE); Uwe Ahr, St. Wendel (DE); Karl-Heinz Schmitt, Freisen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 364 days.

(21) Appl. No.: 10/968,378

(22) Filed: Oct. 18, 2004

(65) Prior Publication Data
US 2005/0147779 A1 Jul. 7, 2005

(30) Foreign Application Priority Data
Oct. 17, 2003 (JP) .................. 103 49 011

(51) Int. Cl.
*F16L 1/00* (2006.01)
*B29C 65/00* (2006.01)
*B32B 37/00* (2006.01)
*B29D 31/00* (2006.01)
*B32B 27/00* (2006.01)
*B29C 47/00* (2006.01)
*B29C 63/00* (2006.01)

(52) U.S. Cl. .............. 156/244.11; 156/182; 156/242; 156/244.13; 156/344; 138/137

(58) Field of Classification Search ............ 156/344, 156/182, 242, 244.11, 244.13; 138/137
See application file for complete search history.

(56) References Cited

U.S. PATENT DOCUMENTS 5,466,322 A 11/1995 Munsch
5,804,151 A 9/1998 Sweetser et al.
5,840,151 A * 11/1998 Munsch .................. 156/380.2
5,928,744 A 7/1999 Heilmann et al.
5,958,167 A 9/1999 Van Driel et al.

FOREIGN PATENT DOCUMENTS

| EP | 0 765 740 | 4/1997 |
| EP | 0765740 | 4/1997 |
| WO | WO92/11820 | 7/1992 |
| WO | WO 95/13918 | 5/1995 |
| WO | WO 96/40512 | 12/1996 |
| WO | WO 98/00286 | 1/1998 |
| WO | WO 02/053359 | 7/2002 |

* cited by examiner

*Primary Examiner*—Philip C Tucker
*Assistant Examiner*—Michael N Orlando
(74) *Attorney, Agent, or Firm*—Kenyon & Kenyon LLP

(57) ABSTRACT

A PVC-free multilayer tube, preferably for medical purposes, with more dependable peelability, comprises at least three layers, of which a base layer comprising a first plastics material has been bonded to at least one connection layer comprising a second plastics material by means of at least one buffer layer arranged between the base layer and the at least one connection layer, the buffer layer comprising a third plastics material, wherein the multilayer tube can be used to mold a coil or a loop with a diameter of down to 50 mm without undesirable kinking. Each of the first and second plastics materials is comprised of at least 25% by weight, based on the total weight of the base layer and the connection layer, respectively, of polyolefins, while the third plastics material has a proportion, based on the total weight of the buffer layer, of more than 75% by weight of a thermoplastic elastomer which is not a polyolefin.

14 Claims, 1 Drawing Sheet

PVC-FREE MULTILAYER TUBE WITH MORE DEPENDABLE PEELABILITY FOR MEDICAL PURPOSES, AND PROCESS FOR ITS PRODUCTION

FIELD OF THE INVENTION

The invention relates to a PVC-free multilayer tube for medical purposes with more dependable peelability, as well as to a tube coil encompassing the multilayer tube and free from undesired kinking. The invention also relates to a process for producing these PVC-free multilayer tubes, and also to the use of the inventive PVC-free multilayer tubes.

BACKGROUND OF THE INVENTION

PVC-free materials (non-PVC materials) and single-layer tubes produced therefrom with only one layer are known, by way of example, from WO 92/11820. This proposes a tube material for medical purposes which comprises a polyurethane polyester blend and which not only can be subjected to a sterilization treatment in an autoclave but also is hot-sealable and capable of high-frequency sealing and hot-frequency welding.

EP 0765740 discloses a PVC-free multilayer tube for medial purposes with at least two layers, of which a base layer A) composed of a first plastics material has been bonded to at least one connection layer B) composed of a second plastics material, where the first plastics material comprises at least one polymer which withstands heat sterilization at $\geq 121°$ C. without distortion, has a Shore D hardness $\leq 32$, which at $\geq 121°$ C. has sufficient residual stress for pressure-fit at a connection point, and from which it is possible to form a coil or a loop with a diameter of down to 60 mm without undesired kinking, while the second plastics material comprises at least one polymer which during heat sterilization at 121° C. under the connection pressure resulting from pressure-fit has a tendency to flow and has a Shore A) hardness $\leq 65$, thus ensuring that at temperatures $\geq 121°$ C. the plastics material has dimensional stability, while that of the second plastics material has been lost. Although the multilayer tube according to EP 0765740 can be used to obtain a flexible tube which is transparent after heat sterilization, which has adequate resistance to kinking, and which can be sealed using tube clamps or the like, and which moreover also has the capability to enter into firm and leakproof bonding to an insert, to a medical bag or to a connector, and indeed in an extremely simple manner during a possible heat sterilization treatment, the tube of EP 0765740 remains unsatisfactory in one respect.

Medical tubes are often shipped in coils. This is a space-saving method of transporting tubes without risk of tangling. Tubes can be held together in coils by threads, wires or clamps. However, in a particularly advantageous method, the outer layers of the tubes have been welded to one another in a peelable manner, so that the tubes form coils. In this embodiment, the coil can simply be pulled apart, with no prior need to release a means of holding, which then becomes waste. This also simplifies handling. The production of these coils welded in a peelable manner is described in U.S. Pat. Nos. 5,466,322 and 5,958,167.

When the coils of a tube according to EP 0765740 are separated, a possible consequence is that not only does the tube release from itself at the peelable weld but a crack is produced in the outer layer and can propagate into the inner layer. In the most disadvantageous case, damage to the tube in this process could be so great that a leak could occur. Particularly at low temperatures and if the coils are opened carelessly, the result can be damage which could render the tube unusable.

SUMMARY OF THE INVENTION

In the light of the disadvantages attending the embodiments described in the above-mentioned publications, it is an object of the invention to provide a tube for medical purposes which has more dependable peelability. This novel tube is to be capable of easy finishing to give coils, and the mutually welded coils are to be capable of easy and reliable mutual release, in particular without impairment of function. At the same time, the novel tube is to be capable of individual matching to many different connector materials or bag materials, in particular based on polypropylene or on polycarbonate. It would moreover be desirable that the novel tube material be capable of secure bonding without additional adhesive promoters or the like. The novel multilayer tube is also to have adequate flexibility, elasticity and softness, and nevertheless to have minimum susceptibility to kinking, and to have a relatively high degree of dimensional rigidity, and to be heat-resistant. Finally, in contact with the fluids usually found in the medical sector, the tube is also intended to avoid any emission of hazardous substances into these fluids, and it is intended to be completely inert with respect to medical solutions. Another object of the invention is to provide a process for the production of this multilayer tube. Another object of the invention is to provide uses of the inventive tube material.

These objects, and others not specified in further detail, are achieved via a PVC-free multilayer tube for medical purposes of the type mentioned at the outset with the features described herein.

DETAILED DESCRIPTION

Figure 1:
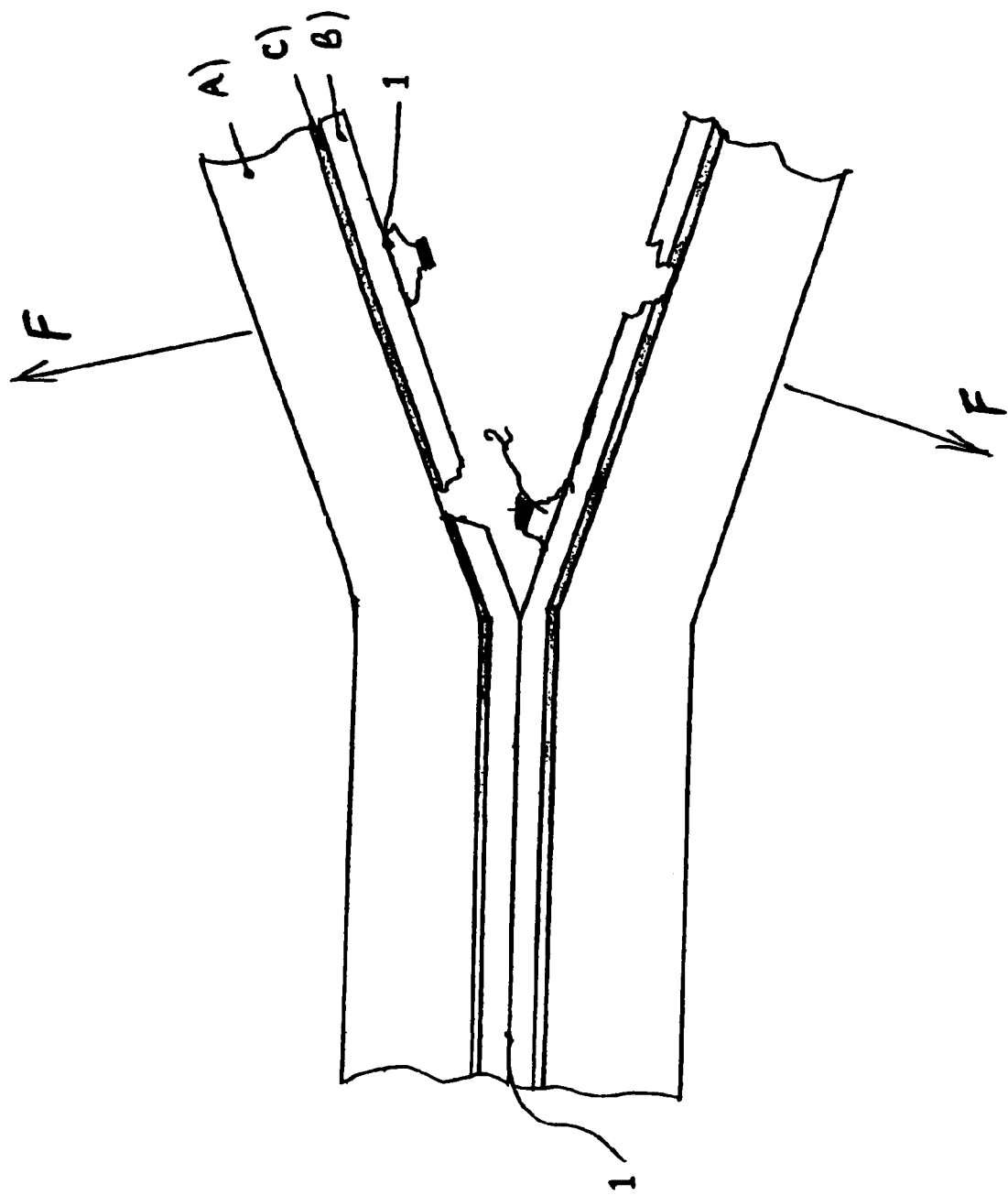
FIG. 1 shows a schematic diagram of an embodiment of a PVC-free multilayer tube according to the present invention.

According to the present invention, a PVC-free multilayer tube for medical purposes with more dependable peelability, where the multilayer tube encompasses at least three layers, of which a base layer A) composed of a first plastics material has been bonded to at least one connection layer B) composed of a second plastics material by means of at least one buffer layer C) arranged between A) and B) and composed of a third plastics material, and where the multilayer tube can be used to form a coil or a loop with a diameter of down to 50 mm without undesirable kinking, and each of the first and the second plastics materials is composed of 25% by weight, or more than 25% by weight, based on the weight of the respective layer A) or B), of polyolefins, while the third plastics material has a proportion, based on the total weight of the layer C), of more 75% by weight of thermoplastic elastomer which is not polyolefin, provides a surprisingly successful method of giving more dependable peelability of a tube coil composed of the multilayer tube.

One of the considerations underlying the present invention is, therefore, introduction of a further buffer layer as middle layer between the base layer or inner layer of a multilayer tube and the connection layer or outer layer. The relatively high elastomer content of the buffer layer makes this substantially softer and mechanically weaker than the base layer and connection layer. This means that the adhesion between the buffer layer and the inner layer or outer layer is therefore also lower. Although the result on opening of the coil can be that the outer layer tears instead of peeling at the weld, the crack generally extends only to the buffer layer and does not propagate into the inner layer. The outer layer, or the buffer layer and the outer layer, delaminate during this process. Because there is no damage here to the inner layer that determines shape, the problem of unusable tubes no longer arises, even at relatively low temperatures.

According to the invention, furthermore, various plastics layers in the inventive multilayer tube material have preferably been matched to one another in such a way that at least one layer functioning as base layer or inner layer gives the tube material sufficient heat resistance during the sterilization, while at least one other layer, functioning as a connection layer or outer layer, can form a secure and leakproof bond to a bag, connector neck, other connector, or another tube, without any need to use additional adhesive, sealant or sealing compositions or auxiliary materials, or other sealing processes (high-frequency energy or the like).

For the purposes of the invention, the term peelability, or more dependable peelability, is particularly important for the quality of the inventive multilayer tubes. For the purposes of the invention, "peelability" or "peel capability" is a property describing the capability of coils of a multilayer tube, sterilized after coiling, to release when exposed to a defined load, when the coils have been welded peripherally at welding temperatures of 400° C. or above. A falling weight is used to apply this load. This method uses a test hammer weighing 5 kg secured to the outermost peripherally welded coil. After 33 cm of free fall, the welded coil is subjected to sudden load. Exposure to the load forcibly opens the coils. If adjacent coils release from one another without loss of function of the tube, the tube is peelable.

The buffer layer C) in the inventive multilayer tube is substantially "more elastic" or "softer" than the base layer A) and the connection layer B). This is a result of the relatively high elastomer content of greater than 75% by weight, preferably greater than or equal to 80% by weight, in the layer C). The proportion of thermoplastic elastomer in the layer C) is particularly advantageously equal to or greater than 90% by weight, and the buffer layer C) is particularly preferably composed or 100% by weight of thermoplastic elastomer, each of the amounts stated being based on the total weight of the layer C). The thermoplastic elastomers which can be used for the layer C) comprise polymeric materials which are not polyolefins.

Polyolefins in the sense of the present description are in the widest sense polymers of the alkenes. Among these are polyalkanes. Examples encompass in particular polymethylene, polyethylenes, such as LDPE, HDPE, LLDPE, mLLDPE, modified polyethylenes, such as XPE, VPE or XLPE, polypropylenes, poly-1-butene and higher poly(alpha-olefin)s. These materials may comprise homopolymers, copolymers, or else block copolymers or random copolymers, and terpolymers. Particular importance is attached to the polymers and copolymers of propylene. Among these are in turn, inter alia, poly(propylenes) polymerized via transition metal catalysts, metallocene polypropylenes, atactic and syndiotactic polypropylenes, and particularly preferably copolymers with ethylene. Among these preference is in turn given to copolymers which have a low ethylene content, for example less than or equal to 5% of ethylene.

Contrasting with the buffer layer C) in which the polyolefin content is restricted to less than 25% by weight, each of the first and the second plastics materials comprises, based on the total weight of the respective layer A) or B), 25% by weight or more than 25% by weight, particularly advantageously more than 30% by weight, of polyolefins. The result is that both the base layer and the connection layer are less elastic than the buffer layer, but are mechanically stronger or more stable than the buffer layer.

Differences can also be observed between the first and the second plastics material with respect to the hardness or softness of the materials. For example, in the multilayer tube of the invention it is preferable for the first plastics material of the base layer to be a relatively hard material. In one particular embodiment, the first plastics material has a Shore D hardness smaller than or equal to 35, particularly preferably smaller than or equal to 32. The second plastics material for the connection layer advantageously comprises a plastics material somewhat softer than the plastics material of the first layer. Materials of particular interest for the invention as the second plastics material are those plastics materials which have a Shore D hardness smaller than or equal to 60. Advantageous materials are those with Shore D smaller than or equal to 55, particularly advantageously smaller than or equal to 50. Shore D >32 is always preferred. Shore D of the second plastics material is particularly preferably >35.

For the purposes of the invention it is also particularly preferred that the third plastics material has a Shore A hardness value smaller than the Shore A hardness value for the second plastics material. Particularly advantageous plastics materials for the buffer layer have a Shore A hardness value <60, in particular <55, and most particularly preferably <50.

There are also differences with respect to the melting point or the glass transition temperature of the different plastics materials used in the various layers of the inventive multilayer tube.

For the purposes of the invention, furthermore, "sterilization" is generally a process for the killing or inactivation (viruses) of all microorganisms including highly resistant spores, and these inventive multilayer tubes in particular withstand steam sterilization in autoclaves using pressurized steam at at least 121° C., corresponding to about one atmosphere above atmospheric pressure, the process known as autoclaving or autoclave treatment, without sustaining any damage.

For the purposes of the invention moreover "plastics material" is in essence composed of constituents which are macromolecular organic compounds, and these plastics materials are also polymers, among which are in particular homopolymers and also copolymers (random copolymers, block polymers and/or graft polymers) and also mixtures (blends) composed of the abovementioned substances.

One criterion for the inventive selection and allocation of a polymer to a plastics material and therefore to a particular functional layer of the multilayer PVC-free tube for medical purposes can also be dimensional stability during heat sterilization.

A plastics material is regarded as dimensionally stable in this sense if a tube specimen of length at least 10 mm and of internal diameter 5 mm and external diameter 7 mm withstands sterilization by superheated steam at 121° C. with a heating time of at least 15 min, a retention time of at least 15 min. and a cooling time of at least 10 min, without visible change in shape, "collapse" or "ovality".

Each of the temperatures stated here is based on the pressure during the steam sterilization, i.e. about one atmosphere above atmospheric pressure. However, the pressure-dependency of the softening point in the range under consideration between atmospheric pressure and the superatmospheric pressure needed for the stream sterilization process is generally negligibly small.

Depending on the desired function of the inventive PVC-free multilayer tube, a layer B) specifically capable of forming bonds may advantageously be arranged only on the outside or both on the outside and on the inside.

Another interior buffer layer (between an interior connection layer B) and the base layer A)) is optional.

A preferred embodiment of the inventive multilayer tube is characterized by a layer sequence A)C)B) or B)A)C)B), in each case from the inside to the outside.

In each case, a tube coil composed of the inventive multilayer tube can be separated without difficulty. In the first case, the inventive tube is intended for introduction into a hollow component whose inner surface is composed of material suitable for forming a bond, while the arrangement of two bonding layers (outside and inside) in the inventive PVC-free multilayer tube permits achievement of one or both of the bonding possibilities mentioned.

In PVC-free multilayer tubes which are particularly advantageous according to the invention and have more dependable peelability, the first plastics material for the inner layer is mostly a synthetic rubber based on isoprene or polypropylene with a density of 0.9 g/cm$^3$, and the second plastics material of the outer layer is mostly a polypropylene copolymer with low ethylene content of about 4%. The buffer layer between these is preferably a SEBS or a mixture of SEBS polymers with styrene content of from 13 to 30%. This combination for each base layer A), outer layer B) and buffer layer C) can itself comply with a wide variety of required properties. Use of polymers according to the following list is preferred for the invention. All percentages stated are percent by weight.

| | |
|---|---|
| Inner layer: | thickness: 900-980 μm for about 1 mm tube wall thickness |
| Blend composed of 50-75% of SIS and | (HVS/3, Kuraray or Hybrar 7125F, Kuraray) |
| 50-25% of RPP | (PP 23M10cs264, REXENE); - PP with Shore D ≦ 32, p = 0.9 g/cm$^3$; (e.g. Adflex 100 G, Himont, with up to 50% rubber content, e.g. PIB styrene-ethylene-butylene rubber, styrene-ethylene-propylene rubber, SIS or (RD204CF, Borealis A/S); PP copolymer |
| Outer layer: | thickness 15-100 μm |
| Blend composed of 50-75% of RPP 25-50% of SIS | (PP 23M10cs264, REXENE or RD 204 CF, Borealis A/S) and (HVS/3, Kuraray or Hybrar 7125 F, Kuraray); |
| Buffer layer: | thickness 10-50 μm |
| 100% of SEBS | (Kraton 1657, Shell) SEBS with 13% of styrene or (Tuftec H 1052, Asahi) SEBS with 20% of styrene or (Tuftec H 1052, Asahi) SEBS with 18% of styrene |
| or 100% of SBS | (Styroflex BX 6105, BASF) SBS with 700 of styrene |
| or a blend composed of 50-90% of SEBS 10-50% of SEBS | (e.g. Kraton G 1726, Shell) and (e.g. Kraton 1625M, Shell) SEBS with 29% of styrene; |

The in detail meanings of the abbreviations are:

| | |
|---|---|
| RPP = | random polypropylene copolymer |
| SIS = | styrene-isoprene-styrene |
| SEBS = | styrene-ethylene-butylene-styrene rubber |
| SBS = | styrene-butylene-styrene rubber |

The adhesion between layers composed of the materials A), B) and C) is in principle sufficient. However, it can advantageously be raised if each of the layers A), B) and/or C) also comprises, based on 100% by weight of their composition as described and defined above, up to 40% by weight of that plastics material used to form one or both adjacent layers of the PVC-free multilayer tube.

This "material compatibilization" or materials substitution markedly raises the compatibility of the layers jointly forming a tube, without placing the other properties at risk.

In a particularly preferred embodiment of the inventive PVC-free multilayer tube, the selection of the plastics materials for all of the layers of the tube is such that they are in essence composed of polyolefin homopolymers or of polyolefin copolymers and modifications thereof (e.g. SEBS). In particular, it was astounding that the invention permits the production of a PVC-free multilayer tube composed exclusively of environmentally compatible materials which permit problem-free formation of bonds to connectors if the steam sterilization process is used and simultaneously comply with all of the other requirements placed upon a tube for use in the medical sector, i.e. in particular better peelability.

The design of the geometry of the tubes themselves may use any of the required and conventional thicknesses and sizes. The inventive PVC-free multilayer tube is preferably composed, based on the entire volume of the tube material, of more than 96-98% by volume of the base layer A). A particularly preferred embodiment of the inventive multilayer tube is characterized in that the base layer A) has a thickness in the range from 800 to 1000 μm. Base layers A) of particular interest have a thickness of >900 μm, preferably of about 910-930 μm, particularly preferably of 920-980 μm. Other embodiments of particular interest for the invention of the multilayer tube are those where the outer layer B) has a thickness in the range from 15 to 100 μm. Particularly preferred outer layers B) or, respectively, connection layers B) have a thickness in the range from 20 to 80 μm, preferably from 30 to 70 μm and particularly preferably about 50 μm. Other multilayer tubes of particular interest for the invention are those in which the buffer layer C) has a thickness of less than 100 μm. In a particularly preferred embodiment of the invention, the multilayer tube of the present invention is characterized in that the buffer layer C) has a thickness in the range from 10 to 30 μm, more particularly preferred is a thickness in the range from about 20 to 30 μm. All of those embodiments of the inventive multilayer tube in which the thickness of the buffer layer C) is smaller than the thickness of the outer layer B) are particularly preferred. The result is more dependable peeling of welded tube coils or of constituents of the tube, without risk of damage to the sensitive inner layer of the tube.

The selection of the layer materials to be coextruded is important for the invention, and it is particularly preferable to select plastics materials or layers in such a way that all of the layers of the PVC-free multilayer tube are in essence composed of polyolefin homopolymers and/or of polyolefin copolymers, or of polymers based thereon, e.g. modified polyolefins (e.g. SEBS, SBS, and the like).

Although the coextrusion of these materials is known in principle, previous experience did not make it foreseeable that a multilayer tube as complex as the inventive tube could be produced satisfactorily. To this extent, the success of the invention was surprising, because otherwise it has constantly been found in industry that, even with the aid of any available tabulated properties of polymers, such as bond strength data, the use of these materials does not necessarily lead to success. That means that in the case of a multilayer coextruded tube it is in principle difficult to achieve a set object purely by selecting from known materials. For example, if rubbers such as SEBS are coextruded with PP it is particularly difficult to match the viscosity of the melt.

If the process according to the present invention is used it is moreover preferably possible to form a PVC-free multilayer tube by selecting the plastics materials in such a way that all of the layers of the tube can also comprise up to 40% by weight of the material of the respective adjacent layer(s). This can provide some compensation for low adhesion between two adjacent layers. Once the product has actually been formed, further operations can be carried out in the usual way on the resultant tube. After it has been formed, it is preferably shock-cooled by water. Because it "freezes" the amorphous state, this method achieves an ideal composite with high flexibility and sufficient stiffness, but the shock-cooling of the melt especially improves the transparency of the tube, because no crystalline regions can form. This gives a low degree of crystallinity and therefore high transparency and toughness.

The inventive PVC-free multilayer tube has excellent suitability for use in the medical sector. The selection of all of the materials of the multilayer tube is such that the tube is transparent, kink-resistant and flexible, and in particular heat-sterilizable and simultaneously capable of secure and bacteria-resistant bonding to an appropriate connector via pressure exerted by the tube. The non-PVC multilayer tube of the invention is also biocompatible. Use of PVC, which always comprises a proportion of plasticizers, is avoided, and there is no need for adhesion promoters, which could in some circumstances diffuse through the layers of plastics material.

Because the properties of the materials of the PVC-free multilayer tube of the invention, and its service properties, are excellent, it can be used with particularly great advantage as a fluid-conveying line in dialysis, infusion or artificial nutrition. To this end, at least the connection region for the connection to the storage bag may advantageously have a welding lip.

Use is especially made here of the compatibility of the connection layer material of the inventive multilayer tube with the connector sections of medical bags (especially composed of polypropylene), and/or with bonding techniques specifically conventional in medical technology, for example in the form of connectors composed of polypropylene. These connectors or bags may have a rough surface over which the inventive PVC-free multilayer tube is pushed, so that the inner surface of the PVC-free multilayer tube with the connection layer B) of the tube pressure-sits on the rough outer surface of the connector or bag (or connector neck of the bag).

The surface of the polypropylene parts, and also the quality of flow of the connection layer B) of the inventive PVC-free multilayer tube, in themselves provide good and secure bonding on exposure to heat, for example during steam sterilization, via flow of the connection layer material into the uneven regions of the surface of the connector or bag neck. The bond becomes even better if the plastics materials used for the production of the connection layer B) of the tube are blended with a proportion, based on 100% by weight of the material of the connection layer, of from 1 to 40% by weight of a plastics material of which the connector or the connector neck of the bag is composed. The bond can be improved by roughening the surface.

Other advantages and details of the invention are apparent from the examples below, which are explained with reference to the figure attached.

FIG. 1 shows the principles of an embodiment of a multilayer tube according to the present invention. In particular, FIG. 1 shows a part of a longitudinal section of two sections which are welded together of a three-layer tube, but each of the two outer layers C) and B) have been omitted in those regions of the longitudinal section of the tube which are not involved in the welding of two layers B).

A) in FIG. 1 indicates the inner layer of an inventive multilayer tube. B) represents the outer layer of an inventive multilayer tube, while C) represents the intermediate layer or buffer layer, arranged between the layers A) and B).

FIG. 1 shows two sections of an inventive multilayer tube, welded together at the surface of the layer B). The weld 1 is obtainable via welding of two sections of the outer layer of the inventive multilayer tube. The schematic diagram shows regions in which the weld between the outer layer B) of the multilayer tube has been opened, while the weld remains intact in other regions where, therefore, two sections or coils of the tube remain welded to one another. Application of a force F acting in the manner indicated by the direction of the arrow on the multilayer tube coils welded to one another causes separation of the two tube coils welded to one another. In this process, the inner layer A) remains completely intact, whereas, as shown by way of example by the numeral 2, if a tear arises in the outer layer B) the result, at the latest beginning at the buffer layer C), is clean separation between the tube coils, without damage. The functional capability of the multilayer tube of the invention can therefore be maintained even if a tear arises in the outer layer. Dependable peeling of the inventive tube is therefore possible.

The invention is further illustrated below using examples of multilayer tubes according to the invention, and in particular experiments relating to the peelability of the inventive tubes are described below.

Table 1 (below) states the composition of the layers of examples of multilayer tubes according to the present invention. In table 1, OL means outer layer, ML means middle layer or in this case buffer layer, and IL means inner layer. All of the materials stated in the first column of the table have been previously compounded and pelletized if they are blends. These are not dry blends. The MFI of blend SA131 was 5.9 (as outer layer), the MFI of blend SI07 was 15 (as buffer layer), the MFI of XM130 was 4.6 (as inner layer). The coils were produced according to the known methods, then welded at the temperatures stated in tables 3 and 4 and sterilized by conventional processes and then stored for four days at the test temperatures stated in tables 3 and 4. The coils were then tested, using the test hammer method described at the outset. The weight of the test hammer was 5 kg and the free-fall height of the hammer was 33 cm. After 33 cm of free fall of the test hammer, the coils are subjected to load and forcibly opened. The test for separability of sterilized tube coils was carried out at various temperatures, namely 23° C., 15° C. and 5° C.

The results of the studies are given in the tables below.

TABLE 1

| Material (% by weight) | Experiment No. | | | | | | | | |
|---|---|---|---|---|---|---|---|---|---|
| | (1.) V40/03 | | | (2.) V41/03 | | | (3.) V42/03 | | |
| | OL 50 μm | ML (PS) 30 μm | IL 920 μm | OL 50 μm | ML (PS) 30 μm | IL 920 μm | OL 50 μm | ML (PS) 30 μm | IL 920 μm |
| RD204CF Co-PP (appr. 4% ethylene), MFI = 9/230° C., Tm = 151° C. | 60 | | 32 | 60 | | 32 | 60 | | 32 |
| Hybrar7125F SIS(20% styrene) MFI = 4/230° C., Tg-ps = 90° C. | 40 | | 68 | 40 | | 68 | 40 | | 68 |
| KratonG1726 SEBS(30% styrene) MFI = 65/? ° C., Tg-ps = 90° C. | | 60 | | | | | | | |
| KratonG1652 SEBS(29% styrene) MFI = 10/? ° C., Tg-ps = 90° C. | | 40 | | | | | | | |
| KratonG1657 SEBS(13% styrene) MFI = 8/? ° C., Tg-ps = 90° C. | | | | | 100 | | | | |
| TuftecH1052 SEBS(20% styrene) MFI = 13/230° C., Tg-ps = 90° C. | | | | | | | | 100 | |
| TuftecH1062 SEBS(18% styrene) MFI = 4.5/230° C., Tg-ps = 90° C. | | | | | | | | | |
| StyroflexBX6105 SBS(70% styrene) MIF = 12.5/230° C., Tg-ps = 90° C. | | | | | | | | | |
| Comments | SA131 | SI07 | XM130 | SA131 | — | XM130 | SA131 | — | XM130 |

| Material (% by weight) | Experiment No. | | | | | |
|---|---|---|---|---|---|---|
| | (4.) V43/03 | | | (5.) V44/03 | | |
| | OL 50 μm | ML (PS) 30 μm | IL 920 μm | OL 50 μm | ML (PS) 30 μm | IL 920 μm |
| RD204CF Co-PP (appr. 4% ethylene), MFI = 9/230° C., Tm = 151° C. | 60 | | 32 | 60 | | 32 |
| Hybrar7125F SIS(20% styrene) MFI = 4/230° C., Tg-ps = 90° C. | 40 | | 68 | 40 | | 68 |
| KratonG1726 SEBS(30% styrene) MFI = 65/? ° C., Tg-ps = 90° C. | | | | | | |
| KratonG1652 SEBS(29% styrene) MFI = 10/? ° C., Tg-ps = 90° C. | | | | | | |
| KratonG1657 SEBS(13% styrene) MFI = 8/? ° C., Tg-ps = 90° C. | | | | | | |
| TuftecH1052 SEBS(20% styrene) MFI = 13/230° C., Tg-ps = 90° C. | | | | | | |
| TuftecH1062 SEBS(18% styrene) MFI = 4.5/230° C., Tg-ps = 90° C. | | | 100 | | | |
| StyroflexBX6105 SBS(70% styrene) MIF = 12.5/230° C., Tg-ps = 90° C. | | | | | 100 | |
| Comments | SA131 | — | XM130 | SA131 | — | XM130 |

TABLE 2

1. Producers of materials:

| Trade name | Material | Producer |
|---|---|---|
| RD204CF | PP copolymer | Borealis A/s |
| Hybrar 7125F | SIS elastomer | Kuraray Co., Ltd |
| KratonG1725 | SEBS elastomer | Shell Chemical Company |
| Kraton1652M | SEBS elastomer | |
| Kraton1657 | SEBS elastomer | |
| TuftecH1052 | SEBS elastomer | Asahi Chemical Industry Co., Ltd |
| TuftecH1062 | SEBS elastomer | |

2. Some properties of the materials

| Trade name | Group | Ethylene or styrene [%] | Tm and Tg [° C.] | MFI [g/10 min] | Shore A |
|---|---|---|---|---|---|
| RD204CF | I | 4 | 151 | 8 | much harder! |
| Hybrar 7125F | II | 20 | 90 & −15 | 4 | 64 |
| KratonG1726 | | 30 | 90 & −45 | 65 | 60 |
| Kraton1652M | | 29 | 90 & −45 | 10 | 75r |
| Kraton1657 | | 13 | 90 & −55 | 8 | 65 |
| TuftecH1052 | | 20 | 90 & −26 | 13 | 67 |
| TuftecH1062 | | 18 | 90 & −32 | 4.5 | 67 |

TABLE 3

| Test Temperature | Type of defect Weld. Temp | Standard* 400° C. | V40 410° C. | V41 410° C. | V42 410° C. | V43 410° C. | V44* 430° C. |
|---|---|---|---|---|---|---|---|
| 5° C. (15 coils in each case) | Complete tear (>10 mm, rupture) | 0 | 0 | 0 | 0 | 350 | 0 |
| | Through-tear (≧1 mm, hole!) | 1 (7%) | 0 | 0 | 0 | 0 | 0 |
| | Severe tear (300μ~<1 mm) | 3 (20%) | 0 | 0 | 0 | 40 | 0 |
| | Slight tear (100μ~300μ) | 8 (53%) | 0 | 0 | 0 | 0 | 0 |
| | Peeling or delamination | 3 (20%) | 15 (100%) | 15 (100%) | 15 (100%) | 15 (100%) | 15 (100%) |
| 16° C. (15 Coils in each case) | Complete tear (>10 mm, rupture) | 0 | 0 | 0 | 0 | 450 | 0 |
| | Through-tear (≧1 mm, hole!) | 2 (13%) | 0 | 0 | 0 | 0 | 0 |
| | Severe tear (300μ~<1 mm) | 3 (20%) | 0 | 0 | 0 | 50 | 0 |
| | Slight tear (100μ~300μ) | 3 (20%) | 0 | 0 | 0 | 0 | 0 |
| | Peeling or delamination | 7 (47%) | 15 (100%) | 15 (100%) | 15 (100%) | 15 (100%) | 15 (100%) |
| 22° C. (15 Coils in each case) | Complete tear (>10 mm, rupture) | 0 | 0 | 0 | 0 | 550 | 0 |
| | Through-tear (≧1 mm, hole!) | 0 | 0 | 0 | 0 | 0 | 0 |
| | Severe tear (300μ~<1 mm) | 0 | 0 | 0 | 0 | 60 | 0 |
| | Slight tear (100μ~300μ) | 9 (60%) | 0 | 0 | 0 | 0 | 0 |
| | Peeling or delamination | 6 (40%) | 15 (100%) | 15 (100%) | 15 (100%) | 15 (100%) | 15 (100%) |

*Standard is based on the tube without buffer layer

TABLE 4

| | | Sterile sample tubes Welding temperature II | | | | | |
|---|---|---|---|---|---|---|---|
| Test Temperature | Type of defect Weld. Temp | Standard* 400° C. | V40 410° C. | V41 410° C. | V42 410° C. | V43 410° C. | V44* 430° C. |
| 5° C. (15 Coils in each case) | Complete tear (>10 mm, rupture) | 0 | 0 | 0 | 0 | 0 | 0 |
| | Through-tear (≧1 mm, hole!) | 1 (7%) | 0 | 0 | 0 | 0 | 0 |
| | Severe tear (300µ~<1 mm) | 3 (20%) | 0 | 0 | 0 | 0 | 0 |
| | Slight tear (100µ~300µ) | 8 (53%) | 0 | 0 | 0 | 0 | 0 |
| | Peeling or delamination | 3 (20%) | 15 (100%) | 15 (100%) | 15 (100%) | 15 (100%) | 15 (100%) |
| 16° C. (15 Coils in each case) | Complete tear (>10 mm, rupture) | 0 | 0 | 0 | 0 | 0 | 0 |
| | Through-tear (≧1 mm, hole!) | 2 (13%) | 0 | 0 | 0 | 0 | 0 |
| | Severe tear (300µ~<1 mm) | 3 (20%) | 0 | 0 | 0 | 0 | 0 |
| | Slight tear (100µ~300µ) | 3 (20%) | 0 | 0 | 0 | 0 | 0 |
| | Peeling or delamination | 7 (47%) | 15 (100%) | 15 (100%) | 15 (100%) | 15 (100%) | 15 (100%) |
| 22° C. (5 Coils in each case) | Complete tear (>10 mm, rupture) | 0 | 0 | 0 | 0 | 0 | 0 |
| | Through-tear (≧1 mm, hole!) | 0 | 0 | 0 | 0 | 0 | 0 |
| | Severe tear (300µ~<1 mm) | 6 (40%) | 0 | 0 | 0 | 0 | 0 |
| | Slight tear (100µ~300µ) | 9 (60%) | 0 | 0 | 0 | 0 | 0 |
| | Peeling or delamination | 6 (40%) | 15 (100%) | 15 (100%) | 15 (100%) | 15 (100%) | 15 (100%) |

*Standard = without buffer layer

What is claimed is:

1. A process for producing a PVC-free multilayer tube free from undesired kinking with more dependable peelability, the process comprising:
    coextruding a first plastics material, a second plastics material, and a third plastics material;
    molding a substantially coaxial and cylindrical multilayer tube during the coextruding, wherein the multilayer tube comprises:
        a base layer bonded to at least one connection layer by at least one buffer layer arranged between the base layer and the at least one connection layer, a thickness of the at least one buffer layer being less than a thickness of the at least one connecting layer;
    wherein the base layer comprises the first plastics material containing polyolefins in an amount of at least 25% by weight of the base layer, the at least one connection layer comprises the second plastics material containing polyolefins in an amount of at least 25% by weight of the at least one connection layer, and the at least one buffer layer comprises the third plastics material containing a modified polyolefin elastomer in an amount of at least 75% by weight of the at least one buffer layer; and
    wherein the multilayer tube can be used to form a coil or a loop with a diameter of down to 50 mm without undesirable kinking; and
    welding the at least one connection layer of the tube to form a peelable coil, such that upon peeling the coil, delamination of the at least one connection layer or delamination of the at least one connection layer and the at least one buffer layer prevents tears from propagating from the at least one connection layer to the base layer.

2. The process according to claim 1, further comprising: shock-cooling the multilayer tube by water after the molding.

3. The process according to claim 1, wherein the polyolefins of the first plastics material and the polyolefins of the second plastics material are a polypropylene having a density $\rho \leqq 0.9$ g/cm$^3$, and wherein the modified polyolefin elastomer is a styrene-ethylene-butylene-styrene rubber or a styrene-butylene-styrene rubber.

4. The process according to claim 1, wherein at least one of the first plastics material and the second plastics material contains polyolefins in an amount of at least 50% by weight, of the base layer for the first plastics material, and of the at least one connection layer for the second plastics material; and wherein the third plastics material contains a modified polyolefin elastomer in an amount of 100% by weight of the at least one buffer layer.

5. The process according to claim 4, wherein the buffer layer has a styrene content of from 13% to 30% by weight of the at least one buffer layer.

6. A process for producing a PVC-free multilayer tube free from undesired kinking with more dependable peelability, the process comprising:
    coextruding a first plastics material, a second plastics material, and a third plastics material;

molding a substantially coaxial and cylindrical multilayer tube during the coextruding, wherein the multilayer tube comprises:
- a base layer bonded to at least one connection layer by at least one buffer layer arranged between the base layer and the at least one connection layer, wherein
  - the base layer includes the first plastics material, the at least one connection layer includes the second plastics material, and the at least one buffer layer includes the third plastics material,
  - the at least one buffer layer has a higher elastomer content than each of a) the base layer and b) the connection layer, and
  - the at least one buffer layer has a thickness that is less than a thickness of the at least one connecting layer; and
- welding the at least one connection layer of the tube to form a peelable coil, such that upon peeling the coil, delamination of the at least one connection layer or delamination of the at least one connection layer and the at least one buffer layer prevents tears from propagating from the at least one connection layer to the base layer.

7. The process according to claim 6, wherein the base layer has a thickness that is at least 800 µm.

8. The process according to claim 6, wherein the volume of the base layer constitutes more than 96% of the entire volume of the tube materials.

9. The process according to claim 6, wherein the at least one buffer layer has an elastomer content of greater than 75% by weight of the at least one buffer layer.

10. The process according to claim 6, wherein the at least one buffer layer has an elastomer content of 100% by weight of the at least one buffer layer.

11. The process according to claim 6, wherein the third plastics material is a styrene-butylene-styrene rubber.

12. A process for producing a PVC-free multilayer tube free from undesired kinking with more dependable peelability, the process comprising:

coextruding a first plastics material, a second plastics material, and a third plastics material;
molding a substantially coaxial and cylindrical multilayer tube during the coextruding, wherein the multilayer tube comprises:
- a base layer bonded to at least one connection layer by at least one buffer layer arranged between the base layer and the at least one connection layer, wherein
  - the base layer comprises the first plastics material, the at least one connection layer comprises the second plastics material, and the at least one buffer layer comprises the third plastics material,
  - the at least one buffer layer is mechanically weaker than each of a) the base layer and b) the connection layer,
  - the at least one buffer layer has a thickness that is less than a thickness of the at least one connecting layer, and the third plastics material is a styrene-butylene-styrene rubber; and
- welding the at least one connection layer of the tube to form a peelable coil, such that upon peeling the coil, delamination of the at least one connection layer or delamination of the at least one connection layer and the at least one buffer layer prevents tears from propagating from the at least one connection layer to the base layer.

13. The process according to claim 12, wherein the first plastics material and the second plastics material each include a polypropylene having a density $\rho \leq 0.9$ g/cm$^3$, or a synthetic rubber based on isoprene, in an amount at least 25% by weight of, respectively, the base layer and the connection layer.

14. The process according to claim 13, wherein the styrene-butylene-styrene rubber is present in an amount of 100% by weight of the at least one buffer layer.

* * * * *

UNITED STATES PATENT AND TRADEMARK OFFICE
CERTIFICATE OF CORRECTION

| | | |
|---|---|---|
| PATENT NO. | : 7,641,753 B2 | |
| APPLICATION NO. | : 10/968378 | |
| DATED | : January 5, 2010 | |
| INVENTOR(S) | : Xiaogang Gao et al. | |

It is certified that error appears in the above-identified patent and that said Letters Patent is hereby corrected as shown below:

On the Title Pg, Item (30), please correct the Foreign Application Priority Data to read as follows:
Oct. 17, 2003   (DE)...........103 49 011

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,641,753 B2 Page 1 of 1
APPLICATION NO. : 10/968378
DATED : January 5, 2010
INVENTOR(S) : Gao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 788 days.

Signed and Sealed this

Sixteenth Day of November, 2010

David J. Kappos
*Director of the United States Patent and Trademark Office*